(12) United States Patent
Gerrish

(10) Patent No.: US 10,278,324 B2
(45) Date of Patent: May 7, 2019

(54) AGBOT FOR ONBOARD TESTING AND DECISION MAKING

(71) Applicant: Steven R. Gerrish, Crawfordsville, IN (US)

(72) Inventor: Steven R. Gerrish, Crawfordsville, IN (US)

( * ) Notice: Subject to any disclaimer, the term of this patent is extended or adjusted under 35 U.S.C. 154(b) by 0 days.

(21) Appl. No.: 15/641,626

(22) Filed: Jul. 5, 2017

(65) Prior Publication Data

US 2017/0295715 A1    Oct. 19, 2017

Related U.S. Application Data

(63) Continuation-in-part of application No. 15/455,958, filed on Mar. 10, 2017.

(60) Provisional application No. 62/306,920, filed on Mar. 11, 2016.

(51) Int. Cl.

| A01B 79/00 | (2006.01) |
| G01N 33/00 | (2006.01) |
| A01B 79/02 | (2006.01) |
| G01N 30/72 | (2006.01) |
| G01N 33/24 | (2006.01) |
| G05D 1/00 | (2006.01) |
| A01M 17/00 | (2006.01) |

(52) U.S. Cl.
CPC ............ *A01B 79/005* (2013.01); *A01B 79/02* (2013.01); *A01M 17/00* (2013.01); *G01N 30/7206* (2013.01); *G01N 33/0098* (2013.01); *G01N 33/24* (2013.01); *G05D 1/0088* (2013.01); *G05D 1/0022* (2013.01)

(58) Field of Classification Search
USPC .......................................................... 701/2
See application file for complete search history.

(56) References Cited

U.S. PATENT DOCUMENTS

| 6,356,830 B1 * | 3/2002 | Adamchuck ......... A01B 79/005 |
| | | 111/118 |
| 8,286,857 B2 | 10/2012 | Covely |
| 9,877,470 B2 * | 1/2018 | Crinklaw ............ A01M 7/0089 |
| 2003/0229435 A1 | 12/2003 | Van Der Lely |
| 2005/0025357 A1 * | 2/2005 | Landwehr ............ A01M 1/026 |
| | | 382/170 |
| 2009/0192040 A1 * | 7/2009 | Grobler .................. A01N 25/04 |
| | | 504/313 |
| 2011/0257850 A1 * | 10/2011 | Reeve ..................... G06Q 10/04 |
| | | 701/50 |
| 2013/0325242 A1 | 12/2013 | Cavender-Bares et al. |
| 2014/0303814 A1 * | 10/2014 | Burema ............... A01B 79/005 |
| | | 701/3 |

(Continued)

OTHER PUBLICATIONS

CBRNE World Staff; FLIR Announces Mobile Griffin G465 Gas Chromatograph-Mass Spectrometer for Chemical Threat ID; http://cbrneworld.com/news/flir_announces_mobile_griffin_g465_gas_chromatograph_mass_spectrometer_for#axzz4avSBOZav Nov. 1, 2016.

(Continued)

*Primary Examiner* — Tyler D Paige
(74) *Attorney, Agent, or Firm* — Barnes & Thornburg LLP

(57) ABSTRACT

An agricultural system can include an agricultural machine having an in-situ sampling of samples for analysis and determination of preferred courses of action based on characteristics of the samples. Options regarding the preferred courses of action can be communicated to a user for selection.

20 Claims, 5 Drawing Sheets

(56) References Cited

U.S. PATENT DOCUMENTS

| | | | |
|---|---|---|---|
| 2015/0319913 A1 | 11/2015 | Foster et al. | |
| 2016/0063420 A1* | 3/2016 | Tomii | G06Q 10/06315 |
| | | | 705/7.24 |
| 2016/0113286 A1* | 4/2016 | Montesinos Segu | C12R 1/25 |
| | | | 504/358 |
| 2017/0021011 A1 | 1/2017 | Kovarik et al. | |
| 2017/0031149 A1 | 2/2017 | Levin et al. | |
| 2017/0035052 A1 | 2/2017 | Becker | |
| 2017/0325444 A1* | 11/2017 | Crinklaw | A01M 7/0089 |
| 2018/0015491 A1* | 1/2018 | Grimm | B05B 12/008 |

OTHER PUBLICATIONS

Jones et al.; Top 10 Plant-parasitic nematodes in molecular plant pathology; Molecular Plant Pathology; 2013 14 (9), 946-961.

Rich et al.; Introduction to Plant Parasitic Nematodes and Their Management; University of Florida; 50 pages, 2013.

Gerald Pilger; The next big disruption in agriculture;Country Guide; May 8, 2017, 10 pages.

Lambert et al.; Introduction to Plant-Parasitic Nematodes; The Plant Health Instructor; University of Illinois; 2002, revised 2009, 17 pages.

* cited by examiner

AGBOT FOR ONBOARD TESTING AND DECISION MAKING

CROSS-REFERENCE TO RELATED APPLICATION

The present application is a continuation-in-part of, and claims the benefit of, and priority to, U.S. Non-Provisional patent application Ser. No. 15/455,958, filed on Mar. 10, 2017, which claims the benefit of, and priority to, U.S. Provisional Application No. 62/306,920, filed on Mar. 11, 2016, the contents of each of which are incorporated herein by reference in their entireties, and at least including those portions related to devices, systems, and methods for agricultural operations and information.

BACKGROUND

The present disclosure relates generally to devices, systems, and methods of agricultural operations, and more specifically to the devices, systems, and methods of automated agricultural operations.

Automated agricultural machines, such as automated tractors, often operate across vast distances far from resources, covered facilities, and/or other infrastructure. Appropriate operation can require consideration of various factors.

SUMMARY

The present disclosure may comprise one or more of the following features and combinations thereof.

According to an aspect of the present disclosure, an automated agricultural system may include an agricultural machine having a chassis configured for driven motion, a sampler for extracting samples from subject material, a control system including a processor for executing instructions to guide the machine chassis to perform automated agricultural operation, and a testing system secured with the chassis. The testing system may be configured to determine characteristics of nematode populations of at least one of the samples.

In some embodiments, the automated agricultural system may include a treatment system including a material handler adapted for controlled distribution of treatment material to the ground. The processor may be configured for determining and executing operation of the material handler according to the determined characteristics of nematode populations of the at least one of the samples.

In some embodiments, the control system may include circuitry for wireless communication with at least one remote device. The processor may be configured for determining and communicating at least two options of operation for selection by an operator. The at least two options may include an option to operate the material handler according to the determined characteristics of nematode populations of the at least of the one samples.

In some embodiments, the processor may be configured for determining and communicating at least two options of operation based on a nematode concentration of the at least one of the samples for selection by an operator. In some embodiments, the testing system may include a gas chromatograph and/or mass spectrometer for analyzing samples (whether extracted above or below ground). In some embodiments, the subject material may include at least one of soil of an agricultural area and plant tissue within the agricultural area. In some embodiments, the testing system may be configured to determine characteristics of nematode populations based on comparison between response data from analysis of the samples and reference information including plant parasitic nematode information.

According to another aspect of the present disclosure, an agricultural system may include an agricultural machine having a chassis configured for driven motion, a sampler for extracting samples from subject material, a control system including a processor for executing instructions to guide the machine chassis to perform automated agricultural operation, and a testing system secured with the chassis. The testing system may be configured to determine characteristics of the subject material based on response data of at least one of the samples.

In some embodiments, the automated agricultural system may include a treatment system including a material handler adapted for controlled distribution of treatment material to the ground. The processor may be configured for determining and executing operation of the material handler according to the determined characteristics of nematode populations of the at least one of the samples.

In some embodiments, the control system may include circuitry for wireless communication with at least one remote device. In some embodiments, the processor may be configured for determining and communicating at least two options of operation for selection by an operator. The at least two options may include an option to operate the material handler according to the determined characteristics of nematode populations of the at least one of the samples.

In some embodiments, the processor may be configured for determining and communicating at least two options of operation based on a nematode concentration of the at least one of the samples for selection by an operator. In some embodiments, the testing system may include a gas chromatograph and/or mass spectrometer for analyzing samples.

In some embodiments, the subject material may include at least one of soil of an agricultural area and plant tissue within the agricultural area. In some embodiments, the testing system may be configured to determine characteristics of nematode populations based on comparison between response data from analysis of the samples and reference information including plant parasitic nematode information.

These and other features of the present disclosure will become more apparent from the following description of the illustrative embodiments.

DETAILED DESCRIPTION OF THE DRAWINGS

Figure 1:
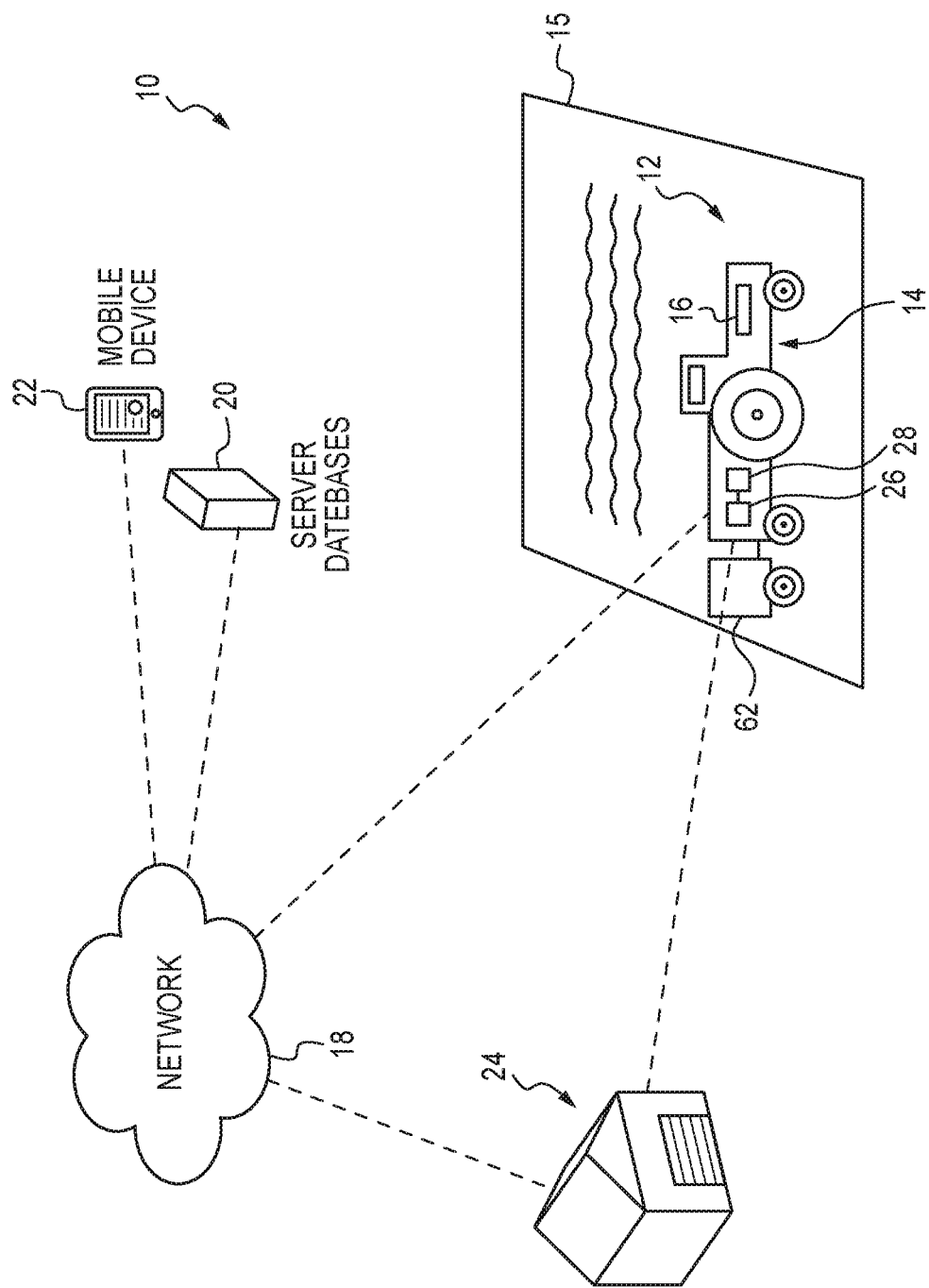
FIG. 1 is a diagrammatic view of an automated agricultural system including an autonomous agricultural machine for performing agricultural operations in communication with various networks, a sampler for extracting test samples from the ground, and a testing system mounted on the chassis for determining characteristics of the samples.

For the purposes of promoting an understanding of the principles of the disclosure, reference will now be made to a number of illustrative embodiments illustrated in the drawings and specific language will be used to describe the same.

Agricultural machines (such as harvesters, planters, and spreaders) are increasingly operated in autonomous or automated modes, whether fully and/or partially. Such automated modes may require little or no direct and/or continuous input by an operator. Moreover, such automated modes may be conducted even without an occupant of the machine (or vehicle). Automation efficiency and effectiveness can be increased by applying useful information in machine decision making. However, availability of useful information, whether real-time, subject-based, and/or otherwise, can be challenging.

The present disclosure includes devices, systems, and methods thereof which can determine, consider, and/or apply, in relatively real-time, characteristics of relevant factors, for example, minerals, nutrients, molecules, solute characteristics, helminths, microbiota and/or other organisms for onsite and/or in-situ diagnostics, treatments, and/or precision decision making. Such devices, systems, and methods include determination, consideration, and/or application of characteristics of a relevant microbiome (or microbiota) in determining courses of action in agricultural applications. A microbiome (or microbiota) is a community of microorganisms which may include bacteria, archaea, protists, fungi, nematodes, and/or viruses. Microbiome information, including identification and/or quantification of nematodes that may feed on portions of the microbiome, can be useful in determining preferred courses of action.

Agricultural devices, systems, and methods within the present disclosure may use characteristics of relevant plant and/or soil microbiome in determining preferred courses of action. Such devices, systems, and methods may include determining the preferred course of action in consideration of end-user microbiome, for example, the microbiome of livestock and/or human consumers of the subject crops. In some embodiments, automated devices, systems, and methods within the present disclosure may independently determine and/or execute preferred operations, but in some embodiments, such automated devices, systems, and methods may determine and/or recommend preferred operations to a user (such as a farmer and/or decision modeler) for consideration and selection. As described herein, automated agricultural devices, systems, and methods can consider actual operational parameters to determine preferred operations based on a relevant microbiome.

An illustrative embodiment of an agricultural system 10 including an agricultural machine 12 is shown in FIG. 1. The agricultural machine 12 illustratively includes a chassis 14 adapted for driven motion. In the illustrative embodiment, the machine 12 is a tractor having a rolling chassis driven by a motor, but in some embodiments, may include any land, air, and/or water capable device. A control system 16 is illustratively mounted to the chassis 14 and guides the machine 12 for agricultural operation. In the illustrative embodiment as shown in FIG. 1, the control system 16 can automated guide the machine 12 without active input by any operator of the machine 12, but in some embodiments, may guide the machine 12 with any of assistive, partial, predominant, and/or full operator input.

As shown in FIG. 1, the agricultural machine 12 is illustratively adapted for guidance to perform agricultural operation by detecting various conditions of its surroundings, for example, current position, speed, elevation, pitch, obstacles, variation in terrain, and by navigating the chassis 14 to negotiate the surroundings while performing its agricultural operation. Navigation of the chassis 14 illustratively includes any of steering, speed and/or throttle control, transmission control and/or other piloting controls (including vehicle specific controls as appropriate according to the embodiment, e.g., for aviation-based vehicles navigation may include flight controls such as position control (e.g., pitch, yaw, rotation, altitude) component control (e.g., flaps), and/or other vehicle-specific local guidance negotiation). The agricultural machine 12 can determine and execute an efficient route according to its agricultural operation. For example, a particular route and/or factors for determining the route may be considered if the agricultural operation includes spreading fertilizing and/or pesticide to a given area.

Referring to FIG. 1, the machine 12 is illustratively arranged in communication with a network 18. The network 18 is illustratively embodied as a wireless network for communications between the machine 12 and various remote systems. For example, the network 18 can provide communications between the machine 12 and various databases 20 and/or mobile devices 22 to assist in decision making. In the illustrative embodiment, the machine 12 is illustratively in communication with a control station 24 embodied as a relatively local communications interface for the machine 12. The machine 12 can illustratively communicate with the network 18 directly and/or through the control station 24. In some embodiments, the control station 24 and/or the network 18 may include hardware and/or software for determining and executing agricultural operation. As discussed in additional detail herein, the network 18 and/or control station 24 can provide remote access to a user (such as a farmer) for decision making regarding agricultural activities of the machine 12.

In the illustrative embodiment as shown in FIG. 1, the agricultural system 10 can perform sample testing relevant to the subject area (illustratively, a section 15 of a farm) for use in decision making. A sampler 26 is illustratively adapted to extract test samples from subject material (e.g., soil) for analysis by a testing system 28. In the illustrative embodiment, the sampler 26 and testing system 28 are each secured with the chassis 14, although in some embodiments, one or more of the sampler 26 and the testing system 28 may be separate from the chassis 14, for example, the testing system 28 may be locally positioned and the machine 12 may transport test samples to the local position of the testing system 28.

In the illustrative embodiment, as shown in FIG. 1, the sampler 26 is embodied as an mechanical soil sampler for extracting precise samples of soil. One example of a suitable soil sampler can include Autoprobe™ as marketed by Autoprobe Technologies, LLC of Little Rock, Ark. In some embodiments, the sampler 26 may be embodied as a mechanical tissue sampler for extracting at least a portion of precise samples from tissue of plants in the subject area, for example, from roots, ground tissue, grain, and/or produce. Suitable tissue samplers may harvest a plant and extract a sample of the tissue (whether partly destructive or non-destructive), and/or may extract one or more samples of the plant tissue without harvesting. Test samples extracted by the sampler 26 are provided to the testing system 28 for analysis. In some embodiments, extracting samples may include preparing soil and/or plant tissue above and/or below ground, for example, using a heated probe and/or aqueous drilling.

Figure 2:
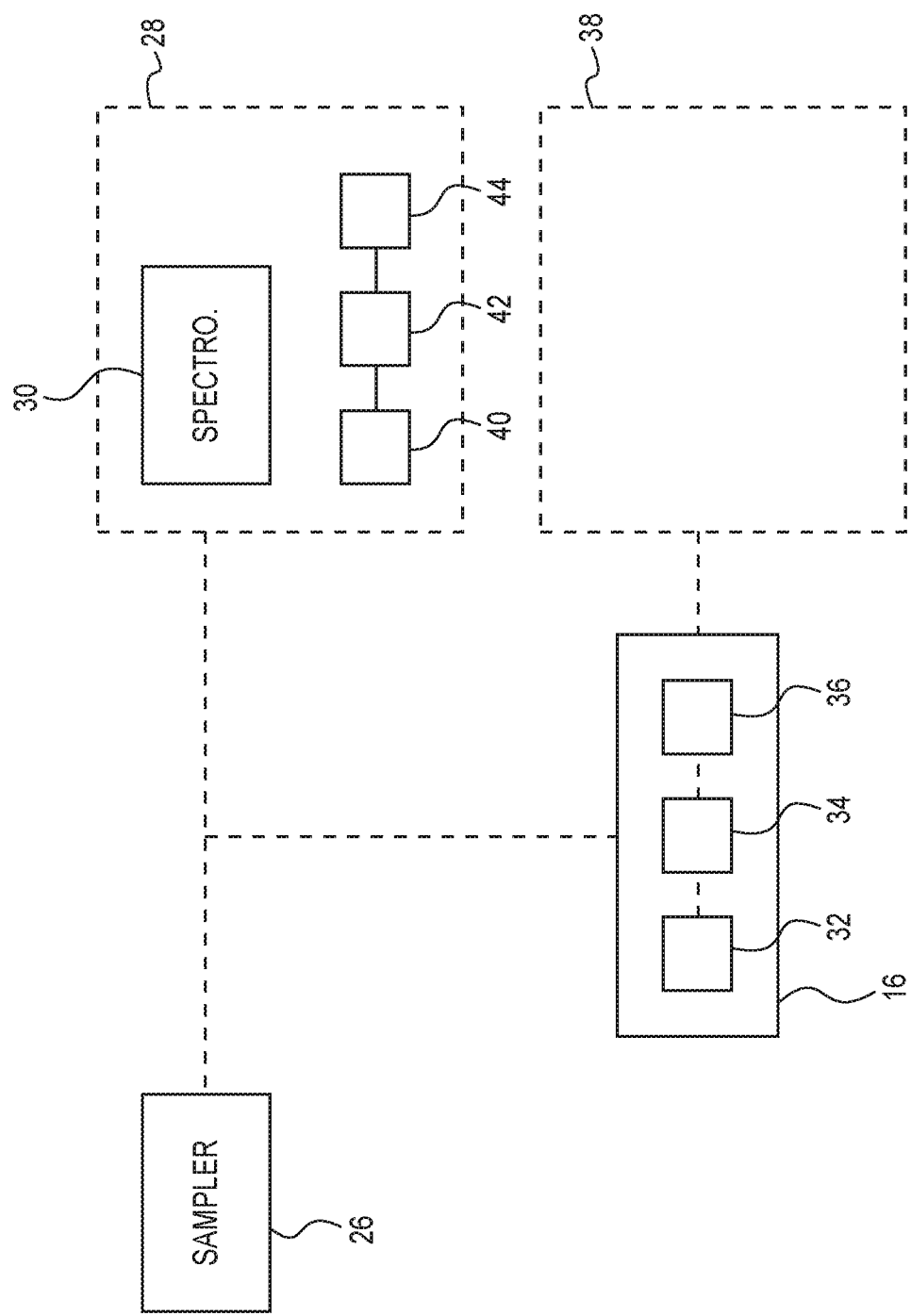
FIG. 2 is a diagrammatic view of various devices of the automated agricultural system of FIG. 1 showing that a control system is in communication with the sampler and the testing system to conduct operations.

Referring to FIG. 2, the testing system 28 is adapted to analyze the samples extracted by the sampler 26 to determine characteristics thereof for decision making. In the illustrative embodiment, the testing system 28 includes a testing device 30 for analyzing the samples. The testing device 30 is adapted to analyze the samples and to yield response data that can be used to identify and/or quantify various characteristics of the sample. Suitable testing devices can include mass spectrometers, for example, a mobile Gas Chromatograph/Mass Spectrometer (GC-MS), such as the Griffin G400's series GC-MS, (GL 410, G460, G465), as marketed by FLIR Systems, Inc. of Wilsonville, Oreg. In some embodiments, any number and/or type of suitable testing devices may be included to analyze the samples. In some embodiments, the sampler and/or testing device may include a heated rod to provide vaporize or liquid ions for passage through the testing device in phase.

In the illustrative embodiment as shown in FIG. 2, the testing system 28 generates response data from analysis of the samples and determines characteristics of the samples based on the response data. The testing system 28 illustratively includes a processor 40 for executing instructions stored on a memory device 42 to determine the nature of plant parasitic nematodes present within the samples. The processor 40 may comprise a quantitative microscopic image recognition analysis device, for example, Parascan using automated microscopy methods, as marketed by Qmira, LLC of Carmel, Ind. The testing system 28 illustratively communicates with other system/devices through communications circuitry 44. In the illustrative embodiment, the testing system 28 includes hardware and/or software for conducting its disclosed operations, but in some embodiments, hardware and/or software may be shared with other components and/or systems. The testing system 28 illustratively communicates the determined characteristics of the samples to the control system 16.

As shown in FIG. 2, the control system 16 is illustratively in arranged in communication with the sampler 26 and the testing system 28. The control system 16 illustratively includes a processor 32 for executing instructions stored on a memory device 34 to determine and execute operational commands through communications circuitry 36. The communications circuitry 36 illustratively includes various receivers and transmitters and other hardware and/or software components for conducting communications, including wireless communications, as disclosed herein. The control system 16 is illustratively in communication with various sensors, cameras, and/or other devices of the agricultural machine 12 adapted to detect the conditions of the surroundings for communication to the control system 16 for automated guidance of the machine 12. In the illustrative embodiment, navigation, guidance, and agricultural operation of the machine 12 is illustratively conducted by the control system 16, but in some embodiments, the machine 12 may include any number of suitable operations systems including hardware and/or software, whether distinct or shared wholly or partly with other systems, for example, an optional navigation system 38 is shown in communication with the control system 16 for determining and executing local (e.g., ground level) navigational control of the machine 12 (such as steering) alone or in collaboration with the control system 16.

Identification and/or treatment of plant parasitic nematodes with relatively real-time response can provide flexible, efficient crop management assistance. In the illustrative embodiment, identification and/or treatment of plant parasitic nematodes is discussed as the central example of diagnostic application for decision making. However, in some embodiments, decision making may be performed on the basis of characteristics of a variety of factors. For example, the testing system 28 may be configured to determine characteristics of any one or more of minerals, molecules, solute characteristics, helminths, microbiota and/or other organisms for onsite and/or in-situ diagnostics, treatments, and/or precision decision making.

Figure 3:
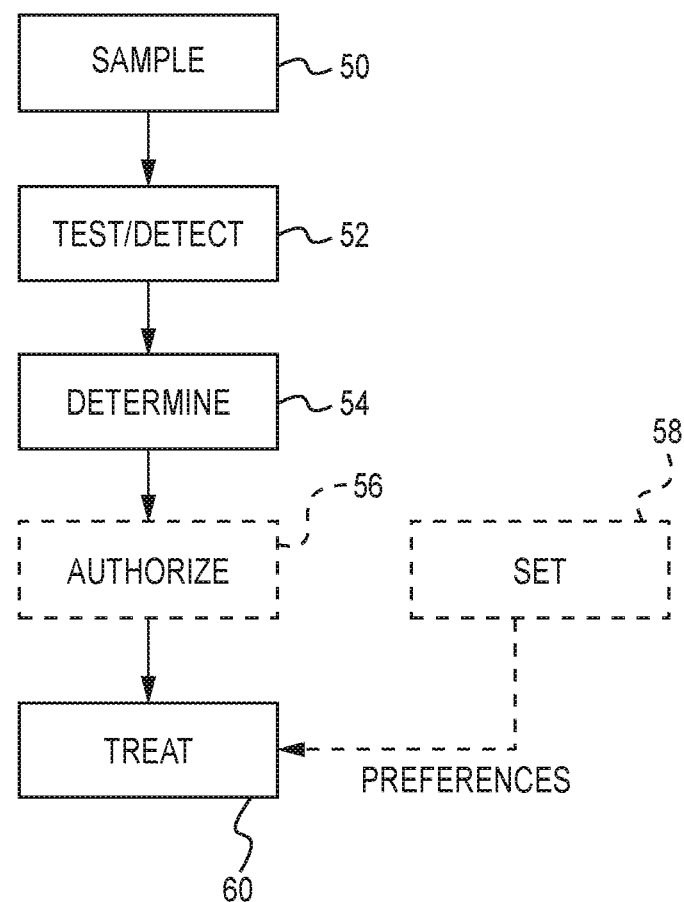
FIG. 3 is a diagram of an operation of the automated agricultural system of FIG. 1.

Referring to FIG. 3, an operational process for decision making is disclosed with respect to boxes 50-60. In boxes 50-60, the agricultural system 10 illustratively conducts sampling, testing, determination, and/or treatment for plant parasitic nematodes. In box 50, sampling is conducted to provide samples for analysis. In box 52, testing is conducted on the samples to provide response data and detection of nematodes is performed. In box 54, response determinations are generated based on the response data. In box 60, treatment can occur according to the response determinations. Optionally, in boxes 56 and 58, authorization and/or pre-settings can be entered for responsive treatments.

In box 50, as shown in FIG. 3, test samples are illustratively extracted. The sampler 26 illustratively extracts test samples, as discussed above. The test samples are illustratively provided to the testing system 28 for analysis. The testing system 28 illustratively conducts testing to detect the presence of plant parasitic nematodes within the test samples. The test system 28 illustratively communicates with the control system 16 to track and store the sample extraction locations such that correspondence and/or controlled handling of test samples can be optionally performed.

In box 52, as shown in FIG. 3, analysis is illustratively conducted as testing and determination. The testing system 28 illustratively conducts testing on the test samples to generate the response data and determines the presence of plant parasitic nematodes based on the generated response data. In the illustrative embodiment, the testing system 28 determines the presence of plant parasitic nematodes by conducting a comparison between the response data and reference information. The processor 40 illustratively conducts comparison according to instructions stored on the memory device 42 between the response data and reference information also stored on the memory device 42. The reference information is illustratively embodied as a reference library including identifying information for various plant parasitic nematodes. In some embodiments, the reference information may include a remote request to a nematologist and/or other expert to assist diagnosis and/or recommend treatment. In some embodiments, the processor 40 may communicate with remote databases to retrieve applicable reference information. Upon detection of plant parasitic nematodes, the processor 40 communicates an indication of their presence to the control system 16 for response determination.

In box 54, as shown in FIG. 3, a preferred course of action is illustratively determined based on indication of the presence of plant parasitic nematodes. The control system 16 illustratively conducts response determinations to determine a preferred course of action based on indication of the presence of plant parasitic nematodes from the testing system 28. In the illustrative embodiment, the control system 16 receives an indication of the presence of plant parasitic nematodes and can determine as a preferred course of action to administer one or more nematicides. The preferred course of action may include one or more options of operation, for example, may determine various recommended nematicide types, application parameters (e.g., amounts, distribution plans, times), and/or whether additional analysis may be beneficial.

In the present example, in box 54, one of the options for the preferred course of action is illustratively selected. The control system 16 illustratively selects one of the options. Optionally, in box 56, the control system 16 may communicate the options of operation for selection by a user, such as a farmer. In one illustrative example, the control system 16 can communicate with either or both of the network 18 and the control station 24 to provide the farmer with the options for selection. In the present example, the farmer can illustratively review the options as displayed on the mobile device 22 which can include various related information, such as stored quantities of nematicides, weather data, factors identified in determining the nematode (shape, size, type, degree of certainty), density of nematodes, historical sampling information, time for execution, pricing information (fuel, nematicide, harvest), etc. Upon farmer selection (authorization) of one of the options, the control system 16 executes the selected option. Additionally and/or alternatively, in box 58, decision making parameters may be preset to assist in any of option determination, option ranking, and/or selection of a preferred course of action with little or no user input. For example, although discussed primarily regarding nematodes, in some embodiments, the testing system 28 may conduct various other soil tests and/or, in collaboration with the control system 16, may determine that certain fertilizers are recommended. In box 58, pre-settings may indicate that fertilizer selections are limited but pre-authorized (for example, pre-settings may require nutrient test levels to be below a predetermined (bottom) threshold before automated treatment), while nematicides may always require farmer selection (authorization). In some embodiments, any suitable number, type, and/or degree of variation in preset parameters may be applied.

In the present example, in box 60, treatment is illustratively conducted. The control system 16 illustratively performs treatment according to the selected option for course of action. For example, if a nematicide is selected, the control system 16 operates a material handler 62 to distribute the nematicide accordingly. The material handler 62 is illustratively embodied as an attachment to the chassis 14 adapted to carry and distribute various materials such as nematicides, fertilizers, insecticides, fungicides, and/or biologicals for application according to the preferred course of action. Accordingly, the agricultural machine 12 can sample, analyze, and treat according to local soil conditions, on-site and/or in relative real time. In some embodiments, treatments may include any suitable operation, whether active (e.g., chemical and/or mechanical treatment, and/or passive (e.g., resting), for example, one of the treatment options may include altering the microbiota by adding and/or controlling organisms to change the outcome for the preferred crop. Among the response data (observations) may include considering the effect of the cover crop interactions with the microbiome and nutrient retentions in the soil profile and altering the planting variety based on these observations and the plant variety genetics. In one non-limiting example, altering the bacterial, fungal, and/or cover crop can work as a nematode control agent. Nematode control may be accomplished by planting a suitable cover crop to inhibit growth and/or adding a bacterial amendment to inhibit growth.

The agricultural system 10 can reduce the time required to conduct soil/plant analysis within a remote lab and can provide more flexible field management. For example, while sampling various portions of a farm including section 15, if it is determined that section 15 requires different treatment than other sections (e.g., significant nematode presence), the machine 12 can treat section 15 according to its local analysis. Such flexibility can improve efficiency and reduce overuse of treatment materials.

As mentioned herein, the various options available for decision making may include a variety of courses of action. The various courses of action may have associated parameters which can be provided to the farmer for decision making. For example, material quantities, treatment requirements, materials pricing, weather, relative locations (e.g., location of subject field relative to store of materials), season, and/or other factors may be directly relevant and/or indirectly relevant to preferred courses of action. Such factors can be made available to the farmer remotely in selecting options.

Figure 4:
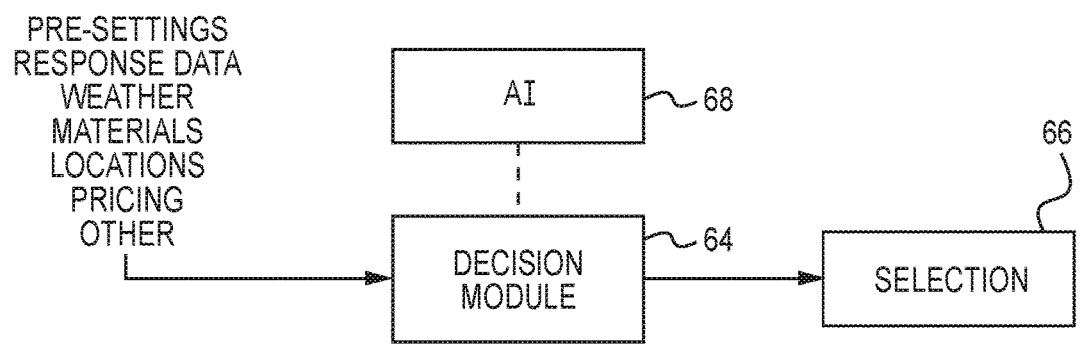
FIG. 4 is a diagram of decision making architecture of the automated agricultural system of FIG. 1.

As shown in FIG. 4, a decision module 64 illustratively conducts decision making. When decision making is conducted without user input, the decision module 64 illustratively provides an output 66 as the selection of the options of operation, as mentioned above, but the output 66 can represent the options provided to the farmer as appropriate. The decision module 64 illustratively can consider any number of various factors in determining the output 66. Optionally, the decision module 64 can include an artificial intelligence (AI) module 68 for determining the preferred course of action, options thereof, and/or related information (e.g., determined probabilities and/or estimated times related to the preferred courses of operation). The decision module 64 and/or the AI module 68 may execute algorithms, utilize lookup tables and/or other reference materials, and/or may conduct predictions based on any of past, present, and/or future data. For example, past treatment options and/or results may be considered. The decision module 64 is illustratively embodied as software based decision platform implemented on the control system 16, but in some embodiments, may include any suitable hardware/software, dedicated/shared, local/remote arrangements for conducting decision making operations.

Figure 5:
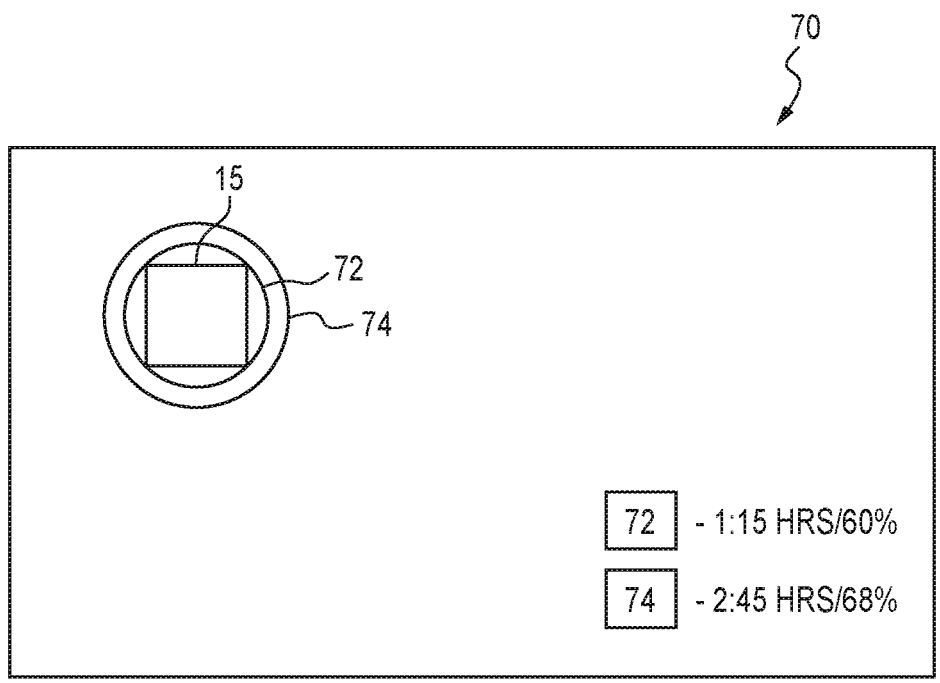
FIG. 5. is an overhead plan view of a graphical display of the automated agricultural system of FIG. 1 showing a field treatment area illustrating the treatment coverage options (circles) and probabilities relative to a subject area (rectangular) as an example of a which may be presented to a user for decision making.

Referring to FIG. 5, the agricultural system 10 may present to the farmer determined probabilities and/or estimated times related to the preferred courses of operation as determined by the decision module 64. The agricultural system 10 may present to the farmer for consideration a predicted likelihood of success particular options for agricultural operations, the available time window of opportunity to complete particular options for agricultural operations before intervening event (e.g., refill, whether event, etc.), and/or other conditions of operation. Likelihood of success relative to plant parasitic nematode presence may include additional options, for example, the control system 16 may provide response data indicating that certain field sections contain plant parasitic nematodes, and the decision module 64 may associate a probability of successfully treating and preventing spread of the parasitic nematodes to other areas.

For example, as shown in FIG. 5, a field 70 includes section 15 which has been determined to include parasitic nematodes. The decision module 64 can present treatment plans 72, 74 including associated probabilities for success, where plan 72 includes a moderate area for application of the nematicide, and plan 74 includes a more liberal area for application. Various treatment plans 72, 74 may be presented as additional options, and may include various parameters for example, material strength (distribution amount), repeated applications, etc. In some embodiments, the user may create custom options by adjusting various parameters and the decision module 64 can determine and provide probabilities associated with the custom options. The decision module 64 can provide predicted health forecasts and timelines based on the various parameters.

The examples and illustrative descriptions of detection of plant parasitic nematode presence, as mentioned above, is one non-limiting example of a relevant sample characteristic for decision making. The testing system 28 may determine other characteristics, for example, identification of plant parasitic nematode types, qualities, and/or quantities. Such characteristics may be determined according to direct detection, such as comparison of observable size, shape, and/or other markers (genomic or otherwise) of nematode organisms, and/or indirect detection, such as prediction based on microbiome composition. Such characteristics can be applied in decision making to obtain more precision in preferred courses of operation and options thereof, for example, nematicide types, strengths, quantities, treatments, coverage areas, among others.

In the illustrative embodiment, operation of the agricultural machine 12 is primarily conducted by the control system 16 mounted on the chassis 14, including determination of preferred courses of action. In some embodiments, the control system 16 may conduct operations in conjunction with control system components not mounted on the chassis 14, for example but without limitation, the control station 24, the network 18 including any server databases 20, as a collective control system. In some embodiments, automated operation of the agricultural machine 12 may be partly or wholly performed by local and/or remote control systems, not mounted on the chassis 14. For example, immediately local decision-making operations, for example but without limitation, steering and/or speed control relative to obstacles along the path of the machine 12 may be performed by the onboard control system 16 (and/or navigation system 38) while global-decision making operations, for example but without limitation, determination of preferred courses of action may be performed by another control system, not onboard the machine 12, and communicated for execution to the control system 16. Collaborative control systems may partly or wholly share software and/or hardware components.

The present disclosure includes using real-time data to provide intelligent solutions to the farmer or autonomous/automated agricultural robots (agbots) for decision making and courses of action considering real time conditions. Relatively real-time information such as test sample response data, market information, resource information, and/or other information (e.g., weather) can be received from information sources whether remote or local to the machine 12.

Operational decisions may include operational-specific determinations. For example but without limitation, an autonomous agricultural machine configured for applying nematicide, fertilizer, and/or pesticide may be operated to vary the amounts of product distribution in consideration of sample response data, and/or an autonomous agricultural machine configured for harvesting (harvest agbot) may be operated in consideration of response data. The present disclosure includes in-situ and/or portable sampling and/or analysis equipment mounted on the chassis 14 for conducting onboard analysis such as soil nutrient sampling, parasite and/or disease identification (e.g., parasitic nematodes, fungus, bacteria, and/or ailments) and/or associated diagnoses, control, and/or treatment operations. Operation of the sampling and analysis equipment may consider weather information (past, present, and/or future), for example but without limitation, in selecting timing, location, technique and/or other characteristics of sampling, analysis, and/or interpretation of data.

In the illustrative embodiment, the test sampler 26, testing system 28, and material handler 62 are embodied as secured with the chassis 14 for operation. In some embodiments, any of the sampler 26, testing system 28, and material handler 62 may be mounted to a chassis of another machine (automated or otherwise) and may be operated independently from machine 12, in communication with any of the control system 16, control station 24, and/or network 18. In some embodiments, the testing system 28 may be locally positioned, whether mobile or relatively stationary, for receiving the samples in transport from the sampler 26.

The present disclosure includes devices, systems, and method for autonomous agricultural system operation which may be applicable to a wide variety of agricultural machines, including but without limitation, harvesters, sorters, spreaders, sprayers, cultivators, tractors, loaders, and irrigators, including whether land, water, and/or air-based. The present disclosure includes devices, systems, and methods for autonomous vehicle in-situ sampling, examination, testing, and/or analysis of macro flora/fauna, micro flora/fauna, minerals/elements, solution characteristics (e.g., pH, cation exchange capacity (CEC), solubility, saturation, etc.) for agricultural decision making. Such devices, systems, and methods may enable precision soil microbiome management including, for example, identifying microscopic minerals, molecules, solute characteristics and organisms for onsite farm diagnostics and memorialization. Such devices, systems, and methods may determine, consider, implement and/or otherwise utilize one or more of factors including pre-planting conditions, growing condition changes, chemical alterations to micro flora/flauna, fertilizer alterations to micro flora/flauna, solute changes in micro flora/flauna, harvest changes to micro flora/flauna, cover crop changes to micro flora/flauna, and mineral extraction and application effects. Such factors may be used for yield management of crops and/or mass customized solutions for livestock and/or humans consuming crops. Genomics of the microbial and micro flora/flauna may be traced through the plant and/or livestock consumption to match the human gut micro flora of individual consumers. In some embodiments, the testing system may determine carbon dioxide ($CO_2$) levels of the test samples, for example, by mass spectrometry or otherwise, as a metabolic measurement of soil health and decomposition by certain organisms and treatment options may be determined based on the $CO_2$ level as response data.

The present disclosure includes devices, systems, and methods for collecting data concerning the nutrients and associated ions in a soil profile and soil solution at the site of sampling; collecting samples of microflora and microfauna, i.e., microbiome, at the same or nearby site and analyzing these samples for identification; determining identification and/or intensity of the nutrients and/or organisms present within samples; determining treatment methods based on the analysis (and related observations) and performing those treatments in a prescription method; communicating related data to a farm manager, network, and/or cloud architecture for automatic observation. Such devices, systems, and method can be performed by operations using intelligent agents or artificial intelligence. The present disclosure includes identifying concentrations of nutrients and/ or micro-constituents in a marine aquaculture environment and taking steps to dilute nutrients and/or treat parasites, such as helminths. In some embodiments, the sampler may acquire samples by any suitable method including drilling a hole in a subject plant, treating the subject plant with compound, and extracting components such as ions, proteins, and/or solute from the drillings material.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. An automated agricultural system, comprising:
    an agricultural machine having a chassis configured for driven motion;
    a sampler for extracting test samples from subject material;
    a control system including a processor for executing instructions to guide the machine chassis to perform automated agricultural operation; and
    a testing system secured with the chassis, the testing system configured to determine characteristics of nematode populations of at least one of the samples, wherein the testing system includes at least one of a gas chromatograph and a mass spectrometer for analyzing samples.

2. The automated agricultural system of claim 1, further comprising a treatment system including a material handler adapted for controlled distribution of treatment material to the ground.

3. The automated agricultural system of claim 2, wherein the processor is configured for determining and executing operation of the material handler according to the determined characteristics of nematode populations of the at least one of the samples.

4. The automated agricultural system of claim 2, wherein the control system includes circuitry for wireless communication with at least one remote device.

5. The automated agricultural system of claim 4, wherein the processor is configured for determining and communicating at least two options of operation for selection by an operator.

6. The automated agricultural system of claim 5, wherein the at least two options includes an option to operate the material handler according to the determined characteristics of nematode populations of the at least of the one samples.

7. The automated agricultural system of claim 1, wherein the processor is configured for determining and communicating at least two options of operation based on a nematode concentration of the at least one of the samples for selection by an operator.

8. The automated agricultural system of claim 7, wherein the subject material includes at least one of soil of an agricultural area and plant tissue within the agricultural area.

9. The automated agricultural system of claim 7, wherein the testing system is configured to determine characteristics of nematode populations based on comparison between response data from analysis of the samples and reference information including plant parasitic nematode information.

10. An agricultural system, comprising:
    an agricultural machine having a chassis configured for driven motion;
    a sampler for extracting test samples from subject material;
    a control system including a processor for executing instructions to guide the machine chassis to perform automated agricultural operation; and
    a testing system secured with chassis, the testing system configured to determine characteristics of the subject material based on response data of at least one of the samples wherein the testing system includes at least one of a gas chromatograph and a mass spectrometer for analyzing samples.

11. The automated agricultural system of claim 10, further comprising a treatment system including a material handler adapted for controlled distribution of treatment material to the ground.

12. The automated agricultural system of claim 11, wherein the processor is configured for determining and executing operation of the material handler according to the determined characteristics of nematode populations of the at least one of the samples.

13. The automated agricultural system of claim 11, wherein the control system includes circuitry for wireless communication with at least one remote device.

14. The automated agricultural system of claim 13, wherein the processor is configured for determining and communicating at least two options of operation for selection by an operator.

15. The automated agricultural system of claim 14, wherein the at least two options includes an option to operate the material handler according to the determined characteristics of nematode populations of the at least one of the samples.

16. The automated agricultural system of claim 10, wherein the processor is configured for determining and communicating at least two options of operation based on a nematode concentration of the at least one of the samples for selection by an operator.

17. The automated agricultural system of claim 7, wherein the subject material includes at least one of soil of an agricultural area and plant tissue within the agricultural area.

18. The automated agricultural system of claim 7, wherein the testing system is configured to determine characteristics of nematode populations based on comparison between response data from analysis of the samples and reference information including plant parasitic nematode information.

19. An automated agricultural system, comprising:
    an agricultural machine having a chassis configured for driven motion;
    a sampler for extracting test samples from subject material;
    a control system including a processor for executing instructions to guide the machine chassis to perform automated agricultural operation; and
    a testing system secured with the chassis, the testing system configured to determine characteristics of nematode populations of at least one of the samples, wherein the processor is configured for determining and communicating at least two options of operation based on a nematode concentration of the at least one of the samples for selection by an operator.

20. An agricultural system, comprising:
    an agricultural machine having a chassis configured for driven motion;
    a sampler for extracting test samples from subject material;
    a control system including a processor for executing instructions to guide the machine chassis to perform automated agricultural operation; and a testing system secured with chassis, the testing system configured to determine characteristics of the subject material based on response data of at least one of the samples, wherein the processor is configured for determining and communicating at least two options of operation based on a nematode concentration of the at least one of the samples for selection by an operator.

* * * * *